United States Patent [19]

Townsend et al.

[11] Patent Number: 5,278,181
[45] Date of Patent: Jan. 11, 1994

[54] SOLUBLE ALKYL[5-[AMINO (PHENYL)METHYL]-1H-BENZIMIDAZOL-2-YL] CARBAMATE ANTHELMINTICS

[75] Inventors: Leroy B. Townsend; Dean S. Wise, both of Ann Arbor, Mich.; Siya Ram, Birmingham, Ala.

[73] Assignee: Board of Regents Acting on Behalf of the University of Michigan, Ann Arbor, Mich.

[21] Appl. No.: 881,910

[22] Filed: May 12, 1992

[51] Int. Cl.$^5$ .................. A61K 31/415; C08D 235/32
[52] U.S. Cl. ................................. 514/395; 548/306.4
[58] Field of Search ...................... 548/306.4; 514/395

[56] References Cited

U.S. PATENT DOCUMENTS 3,657,267  4/1972  Van Gelder .................... 260/309.2
4,435,418  3/1984  Chow ................................. 514/395
4,826,862  5/1989  Raeymaekers et al. ......... 548/306.4

OTHER PUBLICATIONS

"The Synthesis and Chemistry of Certain Anthelmintic Benzimidazoles", by L. B. Townsend & D. S. Wise, in Parasitology Today, vol. 6, No. 4, 1990.

Primary Examiner—Marianne M. Cintins
Assistant Examiner—John Peabody
Attorney, Agent, or Firm—Krass & Young

[57] ABSTRACT

Soluble alkyl [5-(amino (phenyl)methyl)-2H-benzimidazol-2-yl]carbamates, their enantiomorphic forms, and acid addition salts thereof are well absorbed and possess curative anthelmintic activity, especially against filarial worms, when administered orally or parenterally. Pharmaceutical compositions containing the compounds and methods of employing the compounds in methods of treating helminth infections in mammals are also disclosed, together with methods of synthesis.

6 Claims, No Drawings

SOLUBLE ALKYL[5-[AMINO (PHENYL)METHYL]-1H-BENZIMIDAZOL-2-YL] CARBAMATE ANTHELMINTICS

FIELD OF THE INVENTION

The invention relates to novel 5-substituted benzimidazole carbamate ester compounds, methods of their synthesis, pharmaceutical compositions containing the compounds that are useful for the treatment of filarial infections, and methods for treating filarial infections.

BACKGROUND ART

Filariasis comprises a collection of vector-borne worm diseases affecting humans throughout the tropical regions of the world. Worldwide 905 million people are at risk from lymphatic filariasis—caused mainly by *Wuchereria bancrofti* or *Brugia malayi*—90 million of whom are infected; serious cases have to live with the gross deformations of elephantiasis. Similarly 90 million people are at risk from onchocerciasis, 17.6 million of whom are actually infected; of these some 326,000 have lost their sight due to the activities of the microfilariae in the eye.

Drug treatment of filariasis has been unsatisfactory. Diethylcarbamazine has the ability to destroy microfilariae, but unpleasant and sometimes dangerous allergic side effects may occur; it also has the ability in adequate doses to kill adults of lymphatic filariae in some, but far from all patients. Suramin and derivatives of melaminylarsonic acid also have macrofilaricidal action. However, their toxicity, and the fact that they have to be given repeatedly and by injection, make them unsatisfactory candidates for mass treatment. Benzimidazoles, such as flubendazole and mebendazole, are widely used for the treatment of intestinal helminth infections in mammals, but they are poorly absorbed and cause pain and inflammation on injection. Thus, none appears suitable for the mass treatment of filariasis infections. More recently it has been found that ivermectin has outstanding activity against microfilariae, but is without effect on adult worms. Treatment once or twice a year with ivermectin combined with a vector control programme forms the basis of the Onchocerciasis Control Programme in West Africa. While regular control of microfilariae with ivermectin will prevent the development of blindness in onchocerciasis, killing of adult worms would give better control of onchocerciasis, and is essential to prevent the development of pathology in lymphatic filariasis. Therefore, the development of new soluble macrofilaricides which are well absorbed by oral administration and are not irritating upon parental administration is essential for the global management of filariasis.

SUMMARY OF THE INVENTION

In accordance with the preferred compound aspect of the invention, there are provided alkyl 5-substituted benzimidazole carbamate esters and their enantiomorphic forms of the structural formula I, II and III:

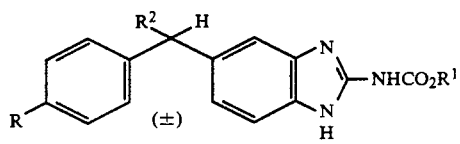

where R is —H or halogen; $R^1$ is lower alkyl; and $R^2$ is halogen or $NH_2$;

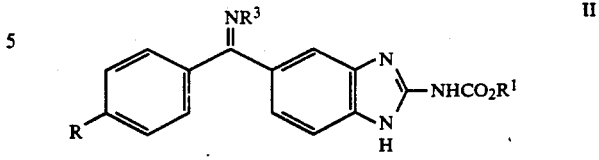

where R is —H or halogen; $R^1$ is lower alkyl; and $R^3$ is $OR^1$, Obenzyl, NHphenyl, or $NHCO_2R^1$; and

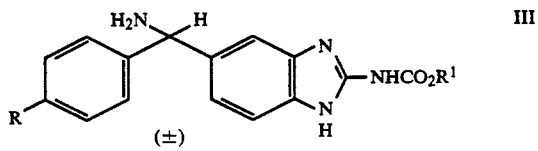

where R is —H or fluorine and $R^1$ is methyl or ethyl or a pharmaceutically acceptable salt thereof.

Preferred compounds having the structural formula III are the following:
methyl (±)-[5-[amino(4-fluorophenyl)methyl]-1H-benzimidazol-2-yl]carbamate;
methyl (+)-[5-[amino(4-fluorophenyl)methyl]-1H-benzimidazol-2-yl]carbamate;
methyl (−)-[5-[amino(4-fluorophenyl)methyl]-1H-benzimidazol-2-yl]carbamate;
methyl (±)-[5-[amino(4-fluorophenyl)methyl]-1H-benzimidazol-2-yl]carbamate, hydrochloride salt;
methyl (±)-[5-[amino (phenyl)methyl]-1H-benzimidazol-2-yl]carbamate;
methyl (+)-[5-[amino (phenyl)methyl]-1H-benzimidazol-2-yl]carbamate;
methyl (−)-[5-[amino (phenyl)methyl]-1H-benzimidazol-2-yl]carbamate;
methyl (±)-[5-[amino (phenyl)methyl]-1H-benzimidazol-2-yl]carbamate hydrochloride salt;
ethyl (±)-[5-[amino(4-fluorophenyl)methyl]-1H-benzimidazol-2-yl]carbamate; and
ethyl (±)-[5-[amino (phenyl)methyl]-1H-benzimidazol-2-yl]carbamate.

Preferred compounds having the structural formula I include compounds of formula III listed above together with the following:
methyl (±)-[5-[chloro(4-fluorophenyl)methyl]-1H-benzimidazol-2-yl]carbamate hydrochloride salt;
methyl (±)-[5-[chloro (phenyl)methyl]-1H-benzimidazol-2-yl]carbamate hydrochloride salt;
ethyl (±)-[5-[chloro (phenyl)methyl]-1H-benzimidazol-2-yl]carbamate hydrochloride salt.

Preferred compounds having the structural formula II are the following:
methyl [5-[(4-fluorophenyl)(methoxyimino)methyl]-1H-benzimidazol-2-yl]carbamate;
methyl [5-[(methoxyimino) phenylmethyl]-1H-benzimidazol-2-yl]carbamate; and
ethyl [5-[(4-fluorophenyl)(methoxyimino)methyl]-1H-benzimidazol-2-yl]carbamate.

The compounds produced in the (±) form can be resolved as their (+) and (−) enantiomorphic optical isomers by per se art-recognized conventional means such as fractional crystallization of salts formed from optically active acids, separation of the isomers by chiral chromatography, or the chiral catalytic reduction of precursors.

The preferred reactions used to synthesize the novel 5-substituted benzimidazole carbamates according to the present invention are outlined in the following REACTION SCHEME.

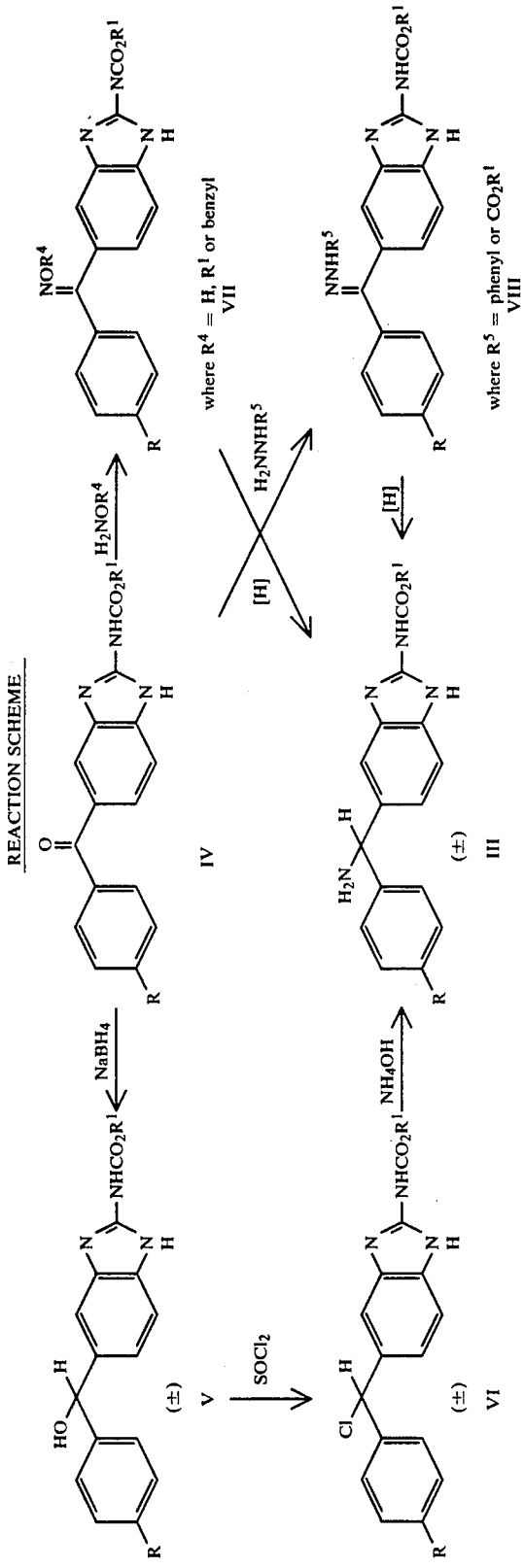

Generally, the reactions can be performed at approximately stoichiometric quantities of the benzimidazole compound and coreactant or with an excess of coreactant. The reaction can be carried out in any non-reactive solvent including (by way of example, but not limited to) benzene, tetrahydrofuran (THF), methanol, glacial acetic acid, trifluoroacetic acid, teriary amides such as N, N-dimethylformamide (DMF), isopropyl alcohol and the like. Advantageously, the reaction medium may also contain added base to serve as an acid binding agent or scavenger such as sodium hydroxide, sodium methoxide, sodium, sodium hydride, or the like. The reactions are normally carried out at temperatures between room temperature and the reflux temperature of the solvent system employed. Preferably, the reaction is carried out at room temperature. The reaction is usually substantially complete within 2 to 4 hours, but in some instances may take several days.

The invention in its first preferred process method aspect is a method of synthesizing alkyl ($\pm$)-[5-[amino (phenyl)methyl]-1H-benzimidazol-2-yl]carbamates of formula III by the reduction of an alkyl [5-[(oxyimino) phenylmethyl]-1H-benzimidazol-2-yl]carbamate of formula VII where $R^4$ represents hydrogen, $R^1$, or benzyl and R and $R^1$ have the aforementioned significance. The reduction may be accomplished utilizing hydrogen in the presence of a catalyst such as palladium on charcoal or by chemical reduction utilizing zinc powder and acetic acid. The intermediate alkyl [5-(oxyimino) phenylmethyl]-1H-benzimidazol-2-yl]carbamates VII [Sinsheimer, J. E., Giri, A. K., Osorio, S., and Wise, D. S., *Mutation and the Environment*, Part E, pp. 225–234 (1990)] are prepared by the reaction of the appropriate alkyl [5-(benzoyl)-1H-benzimidazol-2-yl]carbamate (IV where R and $R^1$ have the aforementioned significance) (*Janssen Pharmaceutica*, U.S. Pat. No. 3,657,267, Apr. 18, 1972) with hydroxylamine or a substituted hydroxylamine derivative in solvents such as methanol or acetic acid.

The invention in its second preferred process method aspect is a method of synthesizing alkyl ($\pm$)-[5-[amino (phenyl)methyl]-1H-benzimidazol-2-yl]carbamates of formula III by the reduction of a hydrazone derivative VIII (where $R^5$ represents phenyl or $CO_2R^1$) of the appropriate alkyl [5-(benzoyl)-1H-benzimidazol-2-yl]-carbamate (IV where R and $R^1$ have the aforementioned significance) utilizing hydrogen and a catalyst such as palladium on charcoal or by chemical reduction utilizing zinc powder and acetic acid. The intermediate hydrazone derivatives (VIII) can be prepared by allowing the appropriate alkyl [5-(benzoyl)-1H-benzimidazol-2-yl]- carbamate IV to react with phenylhydrazine, benzylhydrazine, or an alkylhydrazinocarboxylate in methanol or an acetic acid medium.

The invention in its third preferred process method aspect is a method of synthesizing alkyl ($\pm$)-[5-[amino (phenyl)methyl]-1H-benzimidazol-2-yl]carbamates of formula III by the amination of the appropriate alkyl ($\pm$)-[5-[chloro (phenyl)methyl]-1H-benzimidazol-2-yl]carbamate of formula VI, where R and $R^1$ have the aforementioned significance, with ammonium hydroxide or ammonia in solvents such as tetrahydrofuran, methanol, or ethanol.

The invention in its fourth preferred process method aspect is a method of synthesizing alkyl ($\pm$)-[5-[chloro (phenyl)methyl]-1H-benzimidazol-2-yl]carbamates of formula VI, where R and $R^1$ have the aforementioned significance, by allowing the appropriate alkyl ($\pm$)-[5- [(phenyl)hydroxymethyl)-1H-benzimidazol-2-yl]carbamates (V, where R and $R^1$ have the aforementioned significance) [Van den Bossche, H., Rochette, F., and Horig, C., *Advances in Pharmacology and Chemotherapy*, 19, pp. 75–77 (1982); Ram, S., *Progress in Medicinal Chemistry*, 25, p. 239 (1988)] to react with thionyl chloride. The reaction is preferably performed by heating with a slight excess of thionyl chloride in an inert organic solvent such as benzene or the like.

In a preferred composition aspect, the invention provides pharmaceutical compositions useful for the treatment of helminth infections in a mammal comprising an anthelmintically effective amount of a compound having the structural formula III in combination with a pharmaceutically acceptable carrier.

The invention also provides pharmaceutical compositions useful for the treatment of filarial infections in a mammal comprising an antifilarially effective amount of a compound having the structural formula III in combination with a pharmaceutically acceptable carrier.

In a preferred method aspect, the invention provides methods of treating helminth infections in a mammal comprising administering to a mammal in need of such treatment an anthelmintically effective amount of a compound having the structural formula III in combination with a pharmaceutically acceptable carrier. The invention also provides methods of treating filarial infections in a mammal comprising administering to a mammal in need of such treatment an antifilarially effective amount of a compound having the structural formula III in combination with a pharmaceutically acceptable Carrier.

The alkyl [5-[amino (phenyl)methy]-1H-benzimidazol-2-yl]carbamates of the invention are more soluble than the prior art compounds and thus provide much greater flexibility in the preparation of oral and parenteral pharmaceutical dosage forms (Table 3). For example, in the free base form methyl ($\pm$)-[5-[amino(4-fluorophenyl)methyl]-1H-benzimidazol-2yl]carbamate (Example 1) is soluble in water at 25° C. to the extent of 180 mg/L while the prior art compound methyl [5-(4-fluorobenzoyl)-1H-benzimidazol-2-yl]carbamate is soluble only to the extent of 45 mg/L. Moreover, the compound of Example 1 forms a hydrochloride salt (Example 2) which is more than one-thousand times as soluble (>50,000 mg/L) as the prior art compound.

Acid Addition Salts, Solvates

The compounds of the invention having the structural formula III form pharmaceutically acceptable salts with both organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic, isethionic, lactic, gluconic, glucuronic, sulfamic, benzoic, tartaric, pamoic, and the like. The salts are prepared by contacting the free base form with an equivalent amount of the desired acid in the conventional manner. The free base forms may be regenerated by treating the salt form with a base. For example, dilute aqueous base solutions may be utilized. Dilute aqueous sodium hydroxide, potassium carbonate, ammonium hydroxide, and sodium bicarbonate solutions are particularly suitable for this purpose. The free base forms differ from their respective salt forms somewhat in certain physical properties such as solubility in polar solvents, but the salts are otherwise equivalent to their respective free base forms for purposes of the invention.

The compounds of the invention can exist in unsolvated as well as solvated forms, including hydrated forms. In general, the solvated forms with pharmaceutically acceptable solvents such as water, ethanol and the like are equivalent to the unsolvated forms for purposes of the invention.

Utility; Test Protocols.

The invention in its first anthelmintic pharmaceutical method aspect is a method of treating filarial infections in a mammal comprising administering to a mammal in need of such treatment a filaricidal amount of a compound having the structural formula III in combination with a pharmaceutically acceptable carrier. Filarial parasites which cause disease in mammals include *Brugia pahangi*, *Brugia malayi*, *Acanthocheilonema viteae*, *Wuchereria kalmantani*, *Wuchereria bancrofti*, *Onchocerca volvulus*, *Onchocerca gibsoni*, *Dirofilaria immitis*, and the like.

The invention in its second anthelmintic pharmaceutical method aspect is a method of treating intestinal helminth infections in a mammal comprising administering to a mammal in need of such treatment an anthelmintic amount of a compound having the structural formula III in combination with a pharmaceutically acceptable carrier. Intestinal helminths which cause disease in mammals include *Enterobius vermicularis* (pinworm), *Trichuris trichiura* (whipworm), *Ascaris lumbricoides* (large common roundworm), *Ancylostoma duodenale* (common hookworm), *Necator Americanus* (American hookworm), and *Stronglyoides stercoralis*. The alkyl [5-[amino (phenyl)methyl]-1H-benzimidazol-2-yl]carbamates of the present invention are as contemplated useful in the treatment of helminthic infections in mammals which harbor both filarial and intestinal worms.

The invention in its third anthelmintic pharmaceutical method aspect is a method of treating filarial and intestinal helminth infections in a mammal comprising administering to a mammal in need of such treatment an anthelmintic amount of a compound having the structural formula III in combination with another anthelmintic agent, both in combination with a pharmaceutically acceptable carrier. Other active anthelmintic agents may be combined in the formulation with the compounds including at least one agent selected from diethylcarbamazine, suramin, albendazole, melaminylarsonic acid, flubendazole, levamisole, mebendazole, ivermectin, thiabendazole, fenbendazole, oxibendazole, parbendazole, triclabendazole, cambendazole, amocarzine, pyraclofos, thiophanate, febantil, netobimin, and the like.

Anthelmintic Test Protocol in Jirds

Dual infections of the filarial worms *Brugia pahangi* and *Acanthocheilonema viteae* in jirds are used routinely for antifilarial screening [McCall, J. W., McTier, T. L., and Rowan, S. J., "In vivo models for evaluating potential antifilarial agents", *Onchocerciasis/Filariasis* (Proceedings of a Symposium sponsored by the World Health Organization), Kalamazoo, Mich., Apr. 8-10, 23-24 (1986)].

For this dual infection screen, male Mongolian jirds weighing 50-60 g are infected SC with 10 (5 male and 5 female) adult *A. viteae*, transplanted under sodium pentobarbital anesthesia (48 mg/kg) from donor hamsters infected SC 8 weeks earlier. Two weeks later, 20 (10 male and 10 female) adult *B. pahangi*, taken from donor jirds infected IP 8 weeks earlier, are transplanted into the peritoneal cavity of each jird under sodium pentobarbital anesthesia. After an additional week, when the jirds have acceptable levels of microfilaremia, they are randomly allocated to treatment groups of 3 animals each and a nontreated group of 4-6 animals. Microfilaremia is determined on days 0 (just prior to the first dose), 4 and 56 post-treatment. Unless indicated otherwise, compounds are suspended in hydroxyethylcellulose (0.5%) - Tween 80 (0.1%) and administered SC at 100 mg/kg/day for 5 consecutive days. All jirds are killed on day 56 post-treatment to determine the effects of drugs on adults of *A. viteae* and *B. pahangi*. Live worms are identified as to species, noted as to sex, and counted. The number of dead and/or encapsulated worms is also recorded. A reduction of ≧80% in microfilaremia or ≧50% in adult worm burden (either species) compared with pre-treatment microfilaremia or non-treated control worm burden, respectively, is considered to be significant. For secondary testing with this dual infection screen, groups of 7 animals each are used. For oral dosing, drugs are dissolved or suspended in hydroxyethylcellulose - Tween 80 and administered by gavage.

The antifilarial effects of the alkyl [5-[amino (phenyl)methyl]-1H-benzimidazol-2-yl]carbamates against adult (macro) and immature (micro) filarial worms in the jird are summarized in Table 1 which follows. Compounds described herein in Examples 1 through 3 cured or markedly reduced adult worm burdens of *B. pahangi* and *A. viteae* in jirds when administered subcutaneously at doses ranging from 3.13 to 100 mg/kg/day for 1 to 5 days. Moreover, compounds described in Examples 2 through 4 possessed excellent macrofilaricidal activity when given orally at dosages of 100 or 200 mg/kg/day for 5 days. In addition, compounds described in Examples 2 through 4 possessed a high degree of microfilaricidal activity against immature worms when administered orally or parenterally.

Anthelmintic Test Protocol in beagle Dogs.

Compounds such as methyl (±)-[5-[amino(4-fluorophenyl)methyl]-1H-benzimidazol-2-yl]carbamate (Example 1) and its dihydrochloride hydrate salt (Example 2) which possess outstanding antifilarial activity in jirds by both oral and parenteral routes are then scheduled for secondary evaluation against *Brugia pahangi* infections in beagle dogs utilizing published procedures [McCall, J. W., Dzimianski, M. T., and Supakornedej, P., "*Brugia pahangi* in dogs: Basic parasitological data", Abstracts, 38th Annual Meeting of the American Society of Tropical Medicine and Hygiene, Honolulu, Hi., Dec. 10-14, p. 119, (1989); Dzimianski, M. T., McCall, J. W., Townsend, L. B., and Wise, D. S., "The *Brugia pahangi* canine model as a tertiary antifilarial drug screen", Abstracts, Bulletin de la Societe Francaise de Parasitologie 8 (supplt no. 2), p. 1080, (1990)].

The infective larvae of *B. pahangi* were produced and collected as described by McCall [*J. Georgia Entomol. Soc.* 16:283-293, (1981)]. The dogs were given 100 L$_3$ of *B. pahangi* by subcutaneous injection (SC) into the dorsum of each hind paw or 200 L$_3$ in one hind paw (i.e., a total inoculum of 200 L$_3$ per dog).

The dogs were randomly allocated to treatment groups containing 4 dogs. The dogs were divided by sex and ranked by declining baseline microfilarial counts (average count based on the 5 bleedings made before the day of treatment). Those dogs which were amicrofilaremic or had very few microfilariae were excluded from the trial. Of the remaining dogs, those with the highest baseline microfilaremias were assigned to seven-dog replicates. The sex of the dogs within three of the replicates was the same, while the fourth replicate contained dogs of both sexes. The dogs of a given sex with the highest levels of microfilaremia were placed in the same replicate. The next set of dogs of that sex with the next highest levels of microfilaremia was assigned to the next replicate, and so on until all of the replicates were filled. The dogs within each complete replicate were assigned to test groups using a table of random numbers [Ostle and Mensing, Statistics in Research, Third Edition, Iowa State University Press, Ames, Iowa, pp. 560–563, (1975)]. The test groups were likewise assigned to either control or treatment groups using the table of random numbers.

The first day of treatment, day 0, was approximately 144 days after infection. Drugs were administered orally as a 10% suspension in HEC-Tween 80 or in soft gelatin capsules. Drugs were administered intramuscularly or subcutaneously as a 10% suspension in peanut oil or in HEC-Tween 80. Groups of four dogs served in sham-treated controls in each experiment. All of the treatments were given by IM injection in the dorsal lumbar muscles.

All dogs were observed frequently during each day of treatment and daily throughout the remainder of the study for any signs of reactions. In addition, the hair was shaved at the injection sites to facilitate the observation of possible tissue irritation resulting from treatment.

Blood was collected from each dog on days 51, 43, 27, 19, and 5 before treatment to determine baseline microfilaremias and allocate the dogs to treatment groups. Blood was then collected from all dogs on the day before treatment on day −1, on days 7, 10, 14, 21, 28, 35, 42, 49, and 56 days after treatment. All bleedings were done at approximately the same time of day (11:00–12:00 E.S.T.). Two 20-μl blood films were prepared from each sample and stained with giemsa. Microfilarial counts were made from the 2 blood films.

The dogs were euthanized for necropsy either two or six months after the first day of treatment. Just prior to euthanasia, the dogs were given a subcutaneous injection (SC) of a two percent solution of Evans blue into the dorsum of both hind paws in order to help delineate the lymphatic vessels. This was followed at least 30 minutes later with a lethal dose of Fatal-Plus ® (Vortech Pharmaceuticals, Dearborn, Mich.). A limited necropsy was performed on each dog with examination of the afferent and efferent lymphatics of both hindlimbs and the popliteal, inguinal, internal and external iliac, and lumbar lymph nodes. Any live or dead worms seen were removed. These vessels and lymph nodes were removed, teased, and soaked overnight in normal saline to allow any worms to migrate out of the tissues. The condition of the worms, their sex and number, and the location from which they were recovered were noted.

Effectiveness against the adult parasites was determined as follows:

% Reduction =

$$\frac{\text{mean Recovery Controls} - \text{mean Recovery Test } GP \times 100}{\text{mean Recovery Controls}}$$

Effectiveness against microfilariae for a given day after treatment was determined as follows:

% Reduction =

$$\frac{\text{mean } mf \text{ Controls} - \text{mean } mf \text{ Test Group} \times 100}{\text{mean } mf \text{ Controls}}$$

The adult B. pahangi counts and the microfilarial counts were compared using a one way analysis of variance (ANOVA). A logarithmic transformation of the live adult worm counts and the microfilarial counts [ln(count+1)] was done prior to statistical analysis. Significant differences (p<0.05) among the control groups and treatment group in worm counts or microfilaremia levels were identified by Duncan's multiple range test [Biometrics, 11:1–42, (1955)].

As summarized in Table 2, methyl (±)-[5-[amino(4-fluorophenyl)methyl]-1H-benzimidazol-2-yl]carbamate (Example 1) cured dogs of B. pahangi infections in dogs when administered IM over a wide range of doses from 12.5–50 mg/kg/day for 2 to 3 days. This dosage regimen produced no local muscle irritation. The drug was also curative when administered orally. In addition, the dihydrochloride hydrate salt (Example 2) cured dogs of B. pahangi infections when administered orally at a dosage of 200 mg/kg/day (155 mg/kg/day base equivalent) for 1, 3 or 5 days.

Preparation of Pharmceutical Compositions

When being utilized as anthelmintic agents, the compounds of the invention can be prepared and administered in a wide variety of topical, oral, and parenteral dosage forms. It will be clear to those skilled in the art that the following dosage forms may comprise as the active component, one or more compounds having the structural formula III, a corresponding pharmaceutically acceptable salt of any of said compounds, or a mixture of such compounds and/or salts.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 to 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules, can be used as solid dosage forms suitable for oral administration.

Liquid form preparations include solutions, suspensions, and emulsions. As an example may be-mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided component in water with viscous material, i.e., natural or synthetic gums, resins, methyl cellulose, sodium carboxymethyl cellulose, and other well known suspending agents.

Topical preparations include dusting powders, creams, lotions, gels, and sprays. These various topical preparations may be formulated by well-known procedures. See for examples Remington's Pharmaceutical Sciences, Chapter 43, 14th Ed., Mack Publishing Co., Easton, Pa. 18042, U.S.A.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or table itself or it can be the appropriate number of any of these packaged forms.

The quantity of active compound in a unit of preparation may be varied or adjusted from 50 mg to 1000 mg according to the particular application and the potency of the active ingredient.

In therapeutic use as pharmaceutical agents the compounds utilized in the pharmaceutical method of the invention are administered at the initial dosage of about 1.0 mg to about 200 mg per kilogram. A dose range of about 5 mg to about 100 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The active compounds may also be administered parenterally or intraperitoneally. Solutions of the active compound as a free base of pharmaceutically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions or manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), N,N-dimethylacetamide, suitable mixtures thereof, peanut oil, sesame oil, isopropylmyristate-peanut oil, benzyl benzoatecastor oil, cotton-seed oil, ethyl oleate, triacetin, and the like. The proper fluidity can be maintained, for example, by the use of a coating such as lecithin, by the maintenance of the required particle size in the case of dispersion and by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by sterilization, accomplished by filtering. Generally, dispersions are prepared by incorporating the various sterilized active ingredients into a sterile vehicle which contains the basic dispersion medium and the required other ingredients from those enumerated above. In the case of the sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well-known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in unit dosage form for ease of administration and uniformity of dosage. Unit dosage forms used herein refers to physically discrete units suitable as unitary dosages for the mammalian subjects to be treated; each unit containing a predetermined quantity of active material calculated to produce the desired therapeutic effect in association with the required pharmaceutical carrier. The specification for the novel unit dosage forms of the invention are dictated by and directly dependent on a) the unique characteristics of the active material and the particular therapeutic effect to be achieved, and b) the limitation inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in unit dosage form as hereinbefore disclosed. A unit dosage form can, for example, contain the principal active compound in amounts ranging from 50 to about 1000 mg with from about 100 to about 500 mg being preferred. Expressed in proportions, the active compound is generally present in from about 50 to about 500 mg/ml of carrier. In the case of compositions containing supplementary active ingredients, the dosages are determined by reference to the usual dose and the many of administration of the said ingredients. The daily parenteral doses for mammalian subjects to be treated ranges from 1.0 mg/kg to 50 mg/kg. The preferred daily dosage range is 2 mg/kg to 20 mg/kg.

The alkyl (±)-[5-[amino (phenyl)methyl]-1H-benzimidazol-2-yl]carbamates can be formulated in crystalline or amorphous form. Production of amorphous forms is favored by acid-base reprecipitation. In general amorphous forms tend to have increased solubility and are better absorbed. Suitable acids are acetic, propionic, hydrochloric, phosphoric, formic and nitric acids. Suitable bases are alkali and alkaline earth metal hydroxides, sodium methylate or ethylate, ammonium hydroxide, triethylamine and pyridine.

Stabilization of the amorphous forms to prevent conversion to the crystalline forms may be achieved when a stabilizing polymer is used. Suitable stabilizers include a cellulose derivative such as methylcellulose or sodium carboxymethylcellulose, polyvinylpyrrolidone, xanthan gum, pectin, alginate, tragacanth, gum arabic, carrageenan, agar, polysaccharides from microbial sources, arabinogalactan, galactomannan, dextran and the like.

The invention and the best mode of practicing the same are illustrated by the following examples of preferred embodiments thereof.

Melting points were determined with a Thomas Hoover capillary melting point apparatus and are uncorrected. IR spectra were recorded using a Perkin-Elmer 281 spectrophotometer and values are expressed in $cm^{-1}$. $^1H$ NMR spectra were obtained using a Varian EM-360, 60 MHz spectrophotometer and chemical shifts values are reported in parts per million on the $\delta$ scale with tetramethylsilane as the internal reference.

EXAMPLE 1

Methyl (±)-[5-[Amino(4-Fluorophenyl)Methyl]-1H-Benzimidazol-2-yl]Carbamate

Method A

Methyl [5-[(4-fluorophenyl)(methoxyimino)methyl]-1H-benzimidazol-2-yl]carbamate (34.2 g, 0.1 mole) was added to a suspension of 10% Pd/C (1.77 g) in MeOH (400 mL). Methanolic HCl was added to dissolve the compound. The mixture was hydrogenated at 40° C. under 42 psi. After 42 hrs the $H_2$ uptake was 4 psi. Additional 10% Pd/C (5.0 g) was added, and hydrogenation was continued for 24 hrs. Total $H_2$ uptake was 11 psi. The catalyst was removed by filtration. The product was isolated by removing the solvent under reduced pressure, taking the resulting residue up in $H_2O$, filtering, then adjusting the pH to pH 12 with common ammonium hydroxide. The precipitate that was obtained was isolated by filtration, washed with $H_2O$, then dried.

The crude product was suspended in methanol (1.0 L). Methanolic hydrochloric acid (3.2N, 100 mL) was then added and the mixture stirred until a yellow solution was obtained. Activated charcoal was added and the mixture was allowed to stand for 3 hrs with occasional stirring. Filtration through Celite gave a pale yellow solution that was concentrated under reduced pressure to a solid. This was dissolved in $H_2O$ and adjusted to pH 12 with conc. $NH_4OH$ to give the title product as a white precipitate. This was collected by filtration, washed with $H_2O$, then dried at 60° C. under reduced pressure. Yield: 49.0 g (62%). Mp >320° C. $^1H$ NMR (DMSO-$d_6$): $\delta$ 3.71 (s, 3 H, $OCH_3$), 5.20 (bs, 1 H, CH), 7.06-7.44 (m, 7 H, aromatic H).

Method B

Methyl [5-[(4-fluorophenyl)(hydroxyimino)methyl]-1H-benzimidazol-2-yl]carbamate (566.2 g, 1.72 mole) was added to a mixture of glacial acetic acid (4 L) and MeOH (4 L). Zinc powder (281.9 g, 4.31 g-A) was then added. An initial exothermic reaction was noted after 10 min. After stirring for an additional 60 min, the mixture was heated to reflux. Heating was continued for 4 hrs then the mixture was allowed to cool overnight. Excess zinc was removed by filtration through a Celite pad which was washed with $H_2O$ (4 L) and MeOH (2 L) then discarded. The filtrate was made basic (pH>9) with conc. $NH_4OH$ which afforded the title product as a thick precipitate. This was collected by filtration, washed with $H_2O$ (6 L) then dried in vacuo at 60° C. for 4 days. Crude yield: 520.0 g, (96%). The product was purified by dissolving in 4N AcOH (10 L), treating with charcoal, then filtering through Celite. The filtrate was made basic (pH 10) with conc. $NH_4OH$ which precipitated the title product. The product was collected by filtration, washed with $H_2O$ (6 L) then dried in vacuo at 80° C. for 3 days. Yield: 481.7 g (89%). Mp: >340° C.

All flasks were fitted with a condenser and overhead stirrer using a glass stirring rod and teflon paddle. Protection from moisture was accomplished with $CaSO_4$ dry tubes. Pressure equalized addition funnels equipped with teflon metering valve stopcocks were used to add solutions. All melting points are uncorrected.

Method C

Methyl (±)-[5-[chloro(4-fluorophenyl)methyl]-1H-benzimidazol-2-yl]carbamate hydrochloride salt, prepared from methyl (±)-[5[(4-fluorophenyl)hydroxymethyl]-1H-benzimidazol-2-yl]carbamate [Ram, S., *Progress in Medicinal Chemistry*, 25, 233-247 (1988)] by a method similar to Example 3, was allowed to react with ammonium hydroxide by the procedure of Example 3 to give the desired compound.

Yield 45%; mp>315° C.; IR (KBr): 3400, 1725, 1645, 1602, 840, 760. $^1H$-NMR (DMSO-$d_6$): $\delta$ 3.80 (s, 3H, —$OCH_3$), 5.25 (s, 1H, CH—N), 5.55-8.90 (m, 11H, Ar—H, $NH_2$ and NH [exchangeable with $D_2O$]). Analysis calculated for: $C_{16}H_{15}N_4FO_2$ (314.32): C, 61.14; H, 4.81; N, 17.83 and found: C, 61.12; H, 4.82; N, 17.61.

EXAMPLE 2

Methyl (±)-[5-[Amino(4Fluorophenyl)Methyl]-1H-Benzimidazol-2-yl]Carbamate Dihydrochloride Salt Methyl (±)-[5-[amino(4-fluorophenyl)methyl]-1H-benzimidazol-2-yl]carbamate (209 g, 0.67 mole) was suspended in 2.4 L of MeOH containing (1.5 m HCl) of 12N aq HCl and stirred at room temperature for 24 hours and then at 5° C. for 18 hours. The solid was collected by filtration. The salt was recrystallized by suspending the solid in MeOH (3 L) and adding water (250 mL) until a solution was obtained. The solution was filtered through a Celite pad and evaporated to dryness. The solid was again suspended in MeOH then collected by filtration yield: 175 g (66%) of the title dihydrochloride, mp.>315° C.

EXAMPLE 3

Methyl (±)-[5-[Amino (Phenyl)Methyl]-1H-Benzimidazol-2-yl]Carbamate

Thionyl chloride (15-16 mL) was added dropwise to a cold stirred suspension of methyl (±)-[5-[(phenyl)hydroxymethyl]-1H-benzimidazol-2-yl]carbamate [Allan, R. J., and Wastson, T. R., Eur. *J. Drug. Metab.* 8, 373-38 (1983); Gottschall, D. W., Theodorides, V. J., and Wang, R., *Parasitology Today*, 6, 115-124 (1990)], prepared as in Example 7, (5.0 g) in dry benzene (10 mL). After the addition of thionyl chloride, the resulting reaction mixture was stirred and heated at reflux for 1.5-2 hours (a brown thick mass had separated). The solvent was evaporated on a steam bath under reduced pressure, the residue was triturated at room temperature with dry benzene (15 mL), filtered and dried to yield 5.89 g of product; mp 176°-180° C.; IR (KBr): 3500-2500, 1745, 1630-1600, 750, 695-675 cm$^{-1}$; $^1$H-NMR (DMSO-d$_6$+CDCl$_3$): 3.86 (s, 3H, —OCH$_3$), 6.38 (s, 1H, CH—Cl), 6.88-7.97 (m, 9H, Ar—H and NHCO [exchangeable with D$_2$O]), 13.83 (bs, 1H, NH, [exchangeable with D$_2$O]); analysis calculated for C$_{16}$H$_{14}$N$_3$O$_2$Cl·HCl 0.5·H$_2$O (361.229); C, 53.20; H, 4.46; N, 11.63 and found: C, 53.59; H, 4.57; N, 11.43.

The above hydrochloride salt of methyl (±)-[5-[chloro (phenyl)methyl]-1H-benzimidazol-2-yl]carbamate was then suspended in dry tetrahydrofuran (30 mL) and excess ammonium hydroxide was added to this suspension. The resulting reaction mixture was stirred at room temperature for 12 hours. The solvent was then removed and the residue was chromatographed on silica gel 60F$_{254}$ (40 g, 70-230 mesh, column size 1'×1") using CHCl$_3$:CH$_3$OH (95:5) as eluant. Fractions 3 through 12 (20 mL each) upon concentrating on a steam bath under vacuum afforded the title product, yield 22%; mp>232° C.; IR (KBr): 3340, 1718, 1630, 1600, 870, 750, 721, 695 cm$^{-1}$. $^1$H-NMR (DMSO-d$_6$): δ 3.75 (2, 3H, —OCH$_3$); 5.23 (1, 1H, CH—N), 5.60-6.87 (m, 2H, NH$_2$ [exchangeable with D$_2$O]), 6.90-7.83 (m, 9H, Ar—H and NHCO [exchangeable with D$_2$O]). Analysis calculated for C$_{16}$H$_{16}$N$_4$O$_2$: C, 64.85; H, 5.44; N, 18.91 and found: C, 65.03; H, 5.53; N, 18.67.

EXAMPLE 4

Methyl (±)-[5-[Amino (Phenyl)Methyl]-1H-Benzimidazol-2-yl]Carbamate Dihydrochloride Salt Methyl (±)-[5-(aminophenylmethyl)-1H-benzimidazol-2-yl]carbamate (1 g) was suspended in water (5 mL). To this mixture was added aqueous HCl (12N) with stirring to adjust the pH to ph ~2. As stirring was continued the hydrochloride salt precipitated from the solution. The mixture was cooled in an ice bath and the title product as a precipitate was collected by filtration, m.p.>300° C. Yield: 1.05 g (ca. 85%).

EXAMPLE 5

Methyl [5-[(4-Fluorophenyl) (Methoxyimino)Methyl]-1H-Benzimidazol-2-yl]Carbamate Methyl [5-(4-fluorobenzoyl)-1H-benzimidazol-2-yl]carbamate (Janssen Pharmaceutica, U.S. Pat. No. 3,657,267, Apr. 18, 1972) (31.61 g, 0.11 mole) and methoxylamine hydrochloride (0.35 mole) were added to abs. methanol. After heating under reflux for 48 hrs a clear solution was obtained. After 72 hrs this mixture was filtered hot through Celite then allowed to cool to room temperature. Removal of solvent under reduced pressure gave a solid residue. This material was suspended in H$_2$O and adjusted to pH 12 with conc NH$_4$OH. After stirring for 10 min the precipitate was isolated by filtration, washed repeatedly with H$_2$O, then dried at 50° C. under reduced pressure to give the title product as a white solid. Yield: 33.08 g (96%). Mp: 290°-295° C., TLC: Rf=0.66,0.77 (CHCl$_3$—MeOH,10:1,SiO$_2$) syn and anti isomers. IR (KBr): 3350, 2939, 1735 cm$^{-1}$. $^1$H NMR (DMSO-d$_6$): δ 3.73-3.75 (D, 3H, CH$_3$); 3.85-3.87 (d, 3H, CH$_3$); 6.95-7.46 (m, 7H, Ar); 11.74 (brd, s, 2 H, NH).

EXAMPLE 6

Methyl [5-[(4-Fluorophenyl) (Hydroxyimino)Methyl]-1H-Benzimidazol-2-yl]Carbamate Methyl [5-(4-fluorobenzoyl)-1H-benzimidazol-2-yl]carbamate, (581.6 g, 1.86 mole) (Janssen Pharmaceutica, U.S. Pat. No. 3,657,267, Apr. 18, 1972) was suspended in MeOH (15 L) in which hydroxylamine hydrochloride (508.1 g, 7.32 mole) was dissolved. The mixture was heated at reflux (80 hrs) until a clear solution was obtained and the starting material was no longer detected at TLC. After cooling to room temperature, the mixture was filtered to remove undissolved material, and the solvent was removed under reduced pressure to give a solid residue. This material was suspended in H$_2$O (5 L) and adjusted to pH 12 with conc. NH$_4$OH. The title product that was obtained as a precipitate was collected by filtration, washed with H$_2$O, then dried under reduced pressure at 70° C. for 16 hrs. Yield: 620.8 g. TLC Rf=0.4-0.6 (2nd spot), 0.0 (base line material). Mp:>315° C.; 3405, 1725, 1660-1640, 1600, 835, 760 cm$^{-1}$, $^1$H NMR (DMSO-d$_6$): δ 3.78 (s, 3 H, OCH$_3$), 6.70-8.00 (m, 7 H, Ar—H), 11.20 (bs, 1 H, NH), 11.90 (bs, 1 H, OH).

EXAMPLE 7

Methyl (±)-[5-(4-Fluorophenyl)Hydroxymethyl-1H-Benzimidiazol-2-yl]Carbamate a) Methyl [5-(4-fluorobenzoyl)-1H-benzimidazol-2-yl]carbamate (2.0 g, 0.0064 mole) (Janssen Pharmaceutica, U.S. Pat. No. 3,657,267, Apr. 18, 1972) was added to a premixed stirred slurry of sodium borohydride (NaBH$_4$) (1.72, 0.0453 mole) in isopropyl alcohol (20 mL), the resulting reaction mixture was heated at reflux and stirred for 2-3 hours. The reaction mixture was cooled. Thin layer chromatography on silica gel plates in CHCl$_3$:MeOH (9:1) showed the presence of two compounds with one compound being starting material. Therefore, an additional amount of sodium borohydride (1.12 g, 0.03 mole) and isopropyl alcohol (20 mL) were added to the reaction mixture and stirring was continued at reflux temperature for 1 hour. The reaction mixture was then cooled to room temperature and 20-30 mL of an aqueous 10% sodium hydroxide solution was added to obtain a pH of 7.0. The -isopropyl alcohol was removed under reduced pressure. The resulting residue was triturated with 200 mL of water and the insoluble solid, which was a mixture of starting material and product, was removed by filtration. The filtrate was allowed to cool at 5° C. at which time a colorless solid had crystallized. The solid was dissolved in an excess of boiling methanol (600 mL), and the insoluble material was removed by filtration and discarded. The filtrate was concentrated (100 mL) and allowed to cool to room temperature. The solid which had separated from solution was collected by filtration to yield 1.848 g (91.3%); mp>320° C.; IR (KBr): 3400, 1730, 1646, 1600, 845, 775, 752 cm$^{-1}$; $^1$H-NMR (DMSO-d$_6$): δ2.92–3.75 (bs, 1H, NHCO [exchangeable with D$_2$O]); 3.78 (s, 3H, —OCH$_3$), 5.80 (bs, 2H, CH and —OH [exchangeable with D$_2$O]); 6.87–7.88 (m, 7H, Ar—H), 12.77 (bs, 1H, NH [exchangeable with D$_2$O]); analysis calculated for C$_{16}$H$_{14}$N$_3$FO$_3$·0.5 H$_2$O (324.312): C, 59,26; H, 4.66; N, 12.96 and found: C, 59.15; H, 4.57; N, 12.69.

Ethyl (±)-[5-(Hydroxyphenylmethyl)-1H-Benzimidazol-2-yl]Carbamate b) This compound was prepared by a method similar to that of Example 7 a). Yield 92.6%; mp>315° C.; IR (KBr): 3450, 1690, 1635, 1485, 785, 700. $^1$H-NMR (DMSO-d$_6$): δ 1.07 (t, 3H, C—CH$_3$); 3.44 (q, 2H, OCH$_2$), 5.73 (s, 1H, CHO); 6.83–7.61 (m, 8H, Ar—H); analysis calculated for C$_{17}$H$_{17}$N$_3$O$_3$ (311.341): C, 65.57; H, 5.50, N, 13.49 and found: C, 65.06; H, 5.46; N, 12.91.

EXAMPLE 8

Phenylhydrazone of Methyl (5-Benzoyl-1H-Benzimidazol-2yl]Carbamate

A mixture of methyl (5-benzoyl-1H-benzimidazol-2-yl)carbamate (1.0 g, 0.00339 mole) (Janssen Pharmaceutica, U.S. Pat. No. 3,657,267, Apr. 18, 1972) and phenyl hydrazine (1.30 g) in CH$_3$OH (35 mL) and glacial acetic acid (25 mL) was heated at reflux for 2–3 days. The solvent was evaporated on steam bath under vacuum and the residue was diluted with 20 mL of water. The yellow solid which separated, was collected by filtration and dried in air. The solid was purified by column chromatography on silica gel 60F$_{254}$ (36 g, 70–230 mesh, column size 1'×1") using chloroform as the eluant. Fractions 3–10 (15 mL each) on concentration on steam bath under reduced pressure gave the title compound as a very light yellow solid, yield 0.50 g (39%); mp 212° C., IR (KBr): 3395–3300, 1715, 1640, 1595, 740, 685 cm$^{-1}$. $^1$H-NMR (CDCl$_3$): δ 3.63 (s, 3H, —OCH$_3$), 6.5–8.33 (m, 15H, Ar—H) 10–12.00 (bs, 2H, 2×NH exchangeable with D$_2$O]); analysis calculated for C$_{22}$H$_{19}$N$_5$O$_2$·1.75 H$_2$O (416.955): C, 63.39; H, 5.44; H, 16.80 and found: C, 63.36; H, 5.04; N, 16.64.

EXAMPLE 9

Phenylhydrazone of Methyl [5-(4-Fluorobenzoyl)-1H-Benzimidazol-2-yl]Carbamate

The title compound was prepared by the method of Example 8, yield 48%; mp 160°–163°, IR (KBr): 3400, 1730, 1650, 1605, 765, 745, 685, $^1$H-NMR (CDCl$_3$+DMSO-d$_6$): δ 3.83 [s, 3H, —OCH$_3$] 6,43–8.30 [m, 13H, Ar—H and NHCO (exchangeable with D$_2$O)]11.60 [bs, 1H, NH (exchangeable with D$_2$O)]; analysis calculated for C$_{20}$H$_{18}$N$_5$FO$_2$ (403.417): C, 65.50; H, 4.50; N, 17.36 and found: C, 65.57; H, 4.63; N, 17.16.

EXAMPLE 10

N$^2$-Carbomethoxyhydrazone of Methyl (5-Benzoyl-1H-Benzimidazol-2-yl)Carbamate

A solution of methyl (5-benzoyl-1H-benzimidazol-2-yl)carbamate (2.0 g, 0.00677 mole) and methylhydrazinocarboxylate (2.525 g, 0.028 mole) in glacial acetic acid (50 mL) and methanol (70 mL) was heated at reflux and stirred for 33 hours and (a solid was also separated out during the reaction time) then cooled to room temperature. The title product as a solid was collected by filtration and washed with methanol, dried; yield 1.93 g, (80.32%); mp 320° C.; IR (KBr): 3360, 1752, 1640, 1600, 767, 695 cm$^{-1}$. $^1$H-NMR (DMSO-d$_6$): δ 2.76–3.53 (m, 2H, 2×NHCO [exchangeable with D$_2$O]), 3.64 (s, 3H, —OCH$_3$), 3.72 (s,3H, —OCH$_3$), 7.10–7.93 (m, 8H, Ar—H), 8.89 (s, 1H, NH [exchangeable with D$_2$O]); analysis calculated for C$_{18}$H$_{17}$N$_5$O$_4$·0.5 CH$_3$OH (383.385): C, 57.96; H, 5.00; N, 18.27 and found: C, 58.35; H, 4.99; N, 18.25.

EXAMPLE 11

N$^2$-Carboethoxyhydrazone of Methyl (5)benzoyl-1H-Benzimidazol-2yl]Carbamate

This was prepared by the method of Example 10, yield 85%; mp>300° C., IR (KBr): 3360, 1760–20, 1645, 1600, 765, 700 cm$^{-1}$; $^1$H-NMR (CF$_3$COOH+CDCl$_3$): δ 1.37 [t, 3H, C—CH$_3$], 4.43 [1, 2H, —OCH$_2$] 4.05 [s, 3H, —OCH$_3$], 7.26–8.42 [m, 9H, Ar—H and NHCO]; analysis calculated for C$_{19}$H$_{19}$N$_5$O$_4$·0.5 H$_2$O (390.40): C, 58.46; H, 5.16; N, 17.94 and found: C, 58.65; H, 5.18; N, 17.72.

EXAMPLE 12

Methyl (±)-[5-[Amino (Phenyl)Methyl]-1H-Benzimidazol-2yl]Carbamate

The title compound is prepared by reducing either the phenylhydrazone, the N$^2$-carbomethoxyhydrazone, or the N$^2$-carboethoxyhydrazone of methyl (5-benzoyl-1H-benzimidazol-2-yl)carbamate, according to Method A of Example 1.

EXAMPLE 13

Methyl (±)-5-(Amino(4-Fluorophenyl)Methyl)]-1H-Benzimidazol-2yl]Carbamate

The title compound is prepared by reducing the phenylhydrazone of methyl [5-(4-fluorobenzoyl)-1H-benzimidazol-2-yl]carbamate, according to Method A of Example 1.

EXAMPLE 14

Ethyl (±)-5-(Amino (Phenyl)Methyl]-1H-Benzimidazol-2yl]Carbamate

The title compound is prepared from ethyl (±)-[5-(hydroxy (phenyl)methyl)-1H-benzimidazol-2-yl]carbamate by the same method as that of Example 3 except that the ethyl carbamate is used as a starting material in place of the methyl carbamate.

The following representative examples are given as illustrative pharmaceutical compositions utilizing different carriers. In these examples, Example 12 illustrates the use of the compounds of the invention for intramuscular or subcutaneous injection in a lipid vehicle. Example 16 illustrates the use of the compounds of the invention for intravenous or other types of injection into the host animal utilizing aqueous vehicles. Example 17 is directed to an oral syrup preparation, Example 18 to an oral capsule preparation and Example 16 to oral tablets. Example 20 is directed to use of the compounds of the invention in suitable suppositories. For Examples 15 through 20, the ingredients are listed followed by methods of preparing the composition.

EXAMPLE 15

Injectable, Oleaginous Preparation

COMPOUND of Example 1: 125 mg–500 mg
Peanut oil for injection USP, NF q.s.

COMPOUND having 1 to 50 micron particle size range is added to ampoules or vials, the peanut oil is added, and the ampoules or vials are sealed and sterilized.

EXAMPLE 16

Injectable, Aqueous Preparation

COMPOUND of Example 2: 125 mg–500 mg
Water for injection USP q.s.

Compound is dissolved in water and passed through a 0.22 micron filter. The filtered solution is added to ampoules or vials, sealed and sterilized.

EXAMPLE 17

Syrup 250 mg Active ingredient/5 ml syrup
COMPOUND of Example 2: 32 g
Purified water USP: 200 ml
Cherry syrup q.s. or: 1000 ml COMPOUND is dissolved in the water and to this solution the syrup is added with mild stirring.

EXAMPLE 18

Capsules 50 mg, 125 mg, 250 mg, or 500 mg
COMPOUND of Example 1: 500 mg
Lactose USP, Anhydrous q.s. or: 200 g
Sterotex Powder HM: 5 g Combine COMPOUND and the Lactose in a twin-shell blender equipped with an intensifier bar. Tumble blend for two minutes, blend for one minute with the intensifier bar and then tumble blend again for one minute. A portion of the blend is then mixed with the Sterotex Powder, passed through a #30 screen and added back to the remainder of the blend. The mixed ingredients are then blended for one minute, blended with the intensifier bar for 30 seconds and tumble blended for an additional minute. Appropriate sized capsules are filled with 141 mg., 352.5 mg, 705 mg, or 1410 mg of the blend, respectively, for the 50 mg., 125 mg, 250 mg, and 500 mg containing capsules.

EXAMPLE 19

Tablets 50 mg, 125 mg, 250 mg, or 500 mg
COMPOUND of Example 1: 250 g
Corn Starch NF: 200.0 g
Cellulose, Microcrystalline: 46.0 g
Sterotex Powder HM: 4.0 g
Purified Water q.s. or 300.00 ml Combine the cornstarch, the cellulose and COMPOUND together in a planetary mixer and mix for two minutes. Add the water to this combination and mix for one minute. The resulting mix is spread on trays and dried until a moisture level of 1 to 2 percent is obtained. The dried mix is then milled with a Fitzmill through a #RH2B screen at medium speed. The Sterotex Powder is added to a portion of the mix and passed through a #30 screen, and added back to the milled mixture and the total blended for five minutes by drum rolling. Compressed tablets of 150 mg, 375 mg, 750 mg, and 1500 mg, respectively, of the total mix are formed with appropriate sized punches for the 50 mg, 125 mg, 250 mg, or 500 mg containing tablets.

EXAMPLE 20

Suppositories 125 mg, 250 mg or 500 mg per 3 g
COMPOUND of Example 1: 125 mg, 250 mg, 500 mg
Polyethylene Glycol 1540: 1925 mg, 1750 mg, 1400 mg
Polyethylene Glycol 8000: 825 mg, 750 mg, 600 mg Melt the Polyethylene Glycol 1540 and the Polyethylene Glycol 8000 together at 60° C. and dissolve COMPOUND into the melt. Mold this total at 25° C. into appropriate suppositories.

TABLE 1

Antifilarial Effects of Alkyl (±)-[5-[amino(phenyl)methyl]-1H-benzimidazol-2-yl]carbamates Against Adult (macro) and Immature (micro) Filariae in Jirds

| Compound Example | Dosage Mg/kg/day × days, Route* | % Macrofilarial reduction | | % Microfilarial reduction A. viteae | |
|---|---|---|---|---|---|
| | | B. phangi | A. viteae | Day 4 | Day 56 |
| 1 | 25. × 5 SC | 100 | | | |
| | 25. × 5 SC | | 88 | 0 | |
| | 12.5 × 5 SC | 100 | | | |
| | 6.25 × 5 SC | 92 | | | |
| | 1.56 × 5 SC | 16 | | | |
| 2 | 100. × 5 OR | 32 | 80 | 50 | 75 |
| | 75. × 5 OR | 30 | 83 | | |
| | 25. × 5 SC | 100 | 100 | | |
| | 25. × 1 SC | 100 | 96 | | |
| | 12.5 × 5 SC | 100 | 100 | 80 | 100 |
| | 12.5 × 5 SC | 100 | 100 | | |
| | 12.5 × 1 SC | 72 | 83 | | |
| | 6.25 × 5 SC | 96 | 100 | | |
| | 6.25 × 5 SC | 98 | 100 | 83 | 100 |
| | 3.13 × 5 SC | 84 | 74 | | |
| | 3.13 × 5 SC | 88 | 69 | 88 | 100 |
| | 1.56 × 5 SC | 22 | 48 | | |
| 3 | 100. × 5 OR | 52 | 80 | 83 | 83 |
| | 100. × 5 SC | 100 | | | |
| | 25. × 5 SC | 75 | | | |
| | 6.25 × 5 SC | 0 | | | |
| | 1.56 × 5 SC | 23 | | | |
| 4 | 200. × 5 OR | 100 | 100 | 67 | 100 |
| | 100. × 5 OR | 30 | 81 | 91 | 91 |
| | 12.5 × 5 SC | 18 | 31 | 88 | 50 |
| | 6.25 × 5 SC | 14 | 27 | 67 | 67 |
| | 3.13 × 5 SC | 15 | 9 | 75 | 50 |

*SC = subcutaneous; OR = oral

Antifilarial Effects of Methyl (±)-[5-[amino(4-fluorophenyl)methyl]-1H-benzimidazol-2-yl]carbamate (Example 1) and Its Dihydrochloride Hydrate Salt (Example 2) in Beagle Dogs Infected with *Brugia pahangi.*

| Com-pound Example | Route | Dosage Mg/kg/ day × days | Percent reduction Micro-filariae | Percent reduction Macro-filariae | Dogs cured/ Treated |
|---|---|---|---|---|---|
| 1 | PO | 200 bid × 3[a] | 97 | 93 | 1/3[e] |
|   | SC | 50 × 3[a] | 78 | 76 | 1/4 |
|   | IM | 50 × 3[b] | 100 | 100 | 4/4 |
|   | IM | 50 × 3[b] | 99 | 100 | 4/4 |
|   | IM | 50 × 2[b] | 59 | 92 | 2/4 |
|   | IM | 50 × 1[b] | 55 | 85 | 0/4 |
|   | IM | 25 × 3[b] | 72 | 100 | 4/4 |
|   | IM | 12.5 × 3[b] | 76 | 91 | 1/4 |
|   | IM | 6.25 × 3[b] | 50 | 38 | 0/4 |
| 2 | PO | 200(155)bid × 5[c] | 100 | 99 | 5/6[e] |
|   | PO | 200(155)bid × 5[a] | 100 | 100 | 3/3[e] |
|   | PO | 200(155)bid × 3[a] | 71[d] | 90 | 0/3[e] |
|   | PO | 200(155) × 3[a] | 78[d] | 97 | 1/3[e] |
|   | PO | 200(155)bid × 1[a] | 77[d] | 97 | 1/3[e] |
|   | PO | 200(155) × 1[a] | 74[d] | 79 | 1/3[e] |
|   | PO | 100(78)bid × 5[c] | 86 | 23[d] | 0/4 |
|   | PO | 50(34)bid × 5[c] | 89[d] | 71[d] | 0/4 |

[a]Prepared as a 10% suspension in HEC-Tween 80.
[b]Prepared as a 10% suspension in peanut oil.
[c]Administered as a powder in gelatin capsules.
[d]Not significantly (p < 0.05) different from the control.
[e]These dogs were necropsied 6 months after the start of treatment rather than the previous 2 months.
( ) = mg/kg/day free base equivalent.
bid = dosage divided twice daily.
PO = oral; SC = subcutaneous; IM = intramuscular.

TABLE 3

Aqueous Solubility of Methyl (±)-[5-[Amino(4-Fluorophenyl)methyl]-1H-Benzimidazol-2-yl]carbamate (Example 1) and Its Dihydrochloride Salt (Example 2)

| Compound Example | Solubility in H$_2$O at 25° C. (mg/L) |
|---|---|
| 1 | 180 |
| 2 | >50,000 |
| Flubendazole | 45 |

We claim:

1. Alkyl 5-substituted benzimidazole carbamate esters and their enantiomorphic forms of the structural formula I:

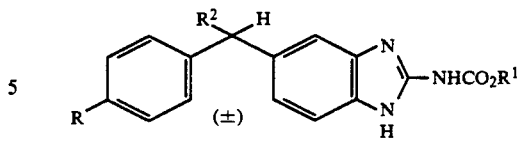

where R is H or halogen; R$^1$ is lower alkyl; and R$^2$ is NH$_2$.

2. Alkyl 5-substituted benzimidazole carbamate esters and their enantiomorphic forms having the structural formula III:

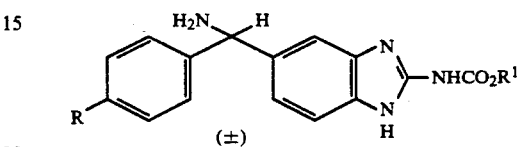

where R is H or fluorine and R$^1$ is methyl or ethyl or a pharmaceutically acceptable salt thereof.

3. A chemical compound defined in claim 2 and selected from the group consisting of:
methyl (±)-[5-[amino(4-fluorophenyl)methyl]-1H-benzimidazol-2-yl]carbamate;
methyl (+)-[5-[amino(4-fluorophenyl)methyl]-1H-benzimidazol-2-yl]carbamate;
methyl (−)-[5-[amino(4-fluorophenyl)methyl]-1H-benzimidazol-2-yl]carbamate;
methyl (±)-[5-[amino(4-fluorophenyl)methyl]-1H-benzimidazol-2-yl]carbamate, hydrochloride salt;
methyl (±)-[5-[amino (phenyl)methyl]-1H-benzimidazol-2-yl]carbamate;
methyl (+)-[5-[amino (phenyl)methyl]-1H-benzimidazol-2-yl]carbamate;
methyl (−)-[5-[amino (phenyl)methyl]-1H-benzimidazol-2-yl]carbamate;
methyl (±)-[5-[amino (phenyl)methyl]-1H-benzimidazol-2-yl]carbamate, hydrochloride salt;
ethyl (±)-[5-[amino(4-fluorophenyl)methyl]-1H-benzimidazol-2-yl]carbamate; and
ethyl (±)-[5-[amino (phenyl)methyl]-1H-benzimidazol-2-yl]carbamate.

4. A pharmaceutical composition useful for the treatment of helminth infections in a mammal comprising an anthelmintic amount of a compound as defined by claim 2 in combination with a pharmaceutically acceptable carrier.

5. A pharmaceutical composition useful for the treatment of filarial infections in a mammal comprising an antifilarial amount of a compound as defined in claim 2 in combination with a pharmaceutically acceptable carrier.

6. A pharmaceutically acceptable acid addition salt of methyl [5-amino(4-fluorophenyl)methyl]-1H-benzimidazol-2-yl]carbamate.

* * * * *

UNITED STATES PATENT AND TRADEMARK OFFICE
CERTIFICATE OF CORRECTION

PATENT NO. : 5,278,181
DATED : January 11, 1994
INVENTOR(S) : Townsend et al.

It is certified that error appears in the above-identified patent and that said Letters Patent is hereby corrected as shown below:

Column 10, line 30, delete "Pharmceutical" and insert --Pharmaceutical--;

Column 13, line 49, after "methoxyimino)" insert -- - --;

Column 14, line 7, delete "(DMSO-$d_6$)" and insert --(DMSO-$\underline{d}_6$)--;

Column 14, line 50, delete "(DMSO-$d_6$)" and insert --(DMSO-$\underline{d}_6$)--;

Column 15, line 14, delete "DMSO-$d_6$" and insert -- (DMSO-$\underline{d}_6$--;

Column 15, line 24, delete "(DMSO-$d_6$)" and insert --(DMSO-$\underline{d}_6$)--;

Column 16, line 15, delete "(DMSO-$d_6$)" and insert --(DMSO-$\underline{d}_6$)--;

Column 16, line 41, delete "(DMSO-$d_6$)" and insert --(DMSO-$\underline{d}_6$)--;

Column 17, line 10, delete "(DMSO-$d_6$)" and insert --(DMSO-$\underline{d}_6$)--;

Column 17, line 26, delete "(DMSO-$d_6$)" and insert --(DMSO-$\underline{d}_6$)--;

UNITED STATES PATENT AND TRADEMARK OFFICE
CERTIFICATE OF CORRECTION

PATENT NO.  : 5,278,181
DATED       : January 11, 1994
INVENTOR(S) : Townsend et al.

It is certified that error appears in the above-identified patent and that said Letters Patent is hereby corrected as shown below:

Column 17, line 63, delete "DMSO-$d_6$)" and insert -- DMSO-$\underline{d}_6$) --

Column 18, line 14, delete "(DMSO-$d_6$)" and insert --(DMSO-$\underline{d}_6$)--;

Column 15, line 24, after "$CDl_3$]:", insert -- δ --;

Column 15, line 54, after "2-yl]", insert -- - --;

Column 16, line 16, delete "(D, 3H, CH3)" and insert --(d, 3H, CH3)--;

Column 16, line 21, after "Hydroxyimino)", insert -- - --;

Column 18, line 6, after "-2-yl)", insert -- - --;

Column 18, line 24, delete "(5)Benzoyl-1H-Benzimidazol-2y1]" and insert --(5)Benzoyl-1H-Benzimidazol-2-yl)--, Column 17, line 34, delete "2yl]" and insert --2-yl]--;

Column 18, line 24, delete "2yl]" and insert --2-yl]--;

Column 18, line 37, delete "2yl]" and insert --2-yl]--;

Column 18, line 47, delete "2yl]" and insert --2-yl]--;

UNITED STATES PATENT AND TRADEMARK OFFICE
CERTIFICATE OF CORRECTION

PATENT NO. : 5,278,181
DATED : January 11, 1994
INVENTOR(S) : Townsend et al.

It is certified that error appears in the above-identified patent and that said Letters Patent is hereby corrected as shown below:

Column 18, line 56, delete "2yl]" and insert --2-yl]--;

Column 18, line 45, delete "(±)-5-(" and insert --(±)-[5- --;

Column 18, line 54, delete "Ethyl (±)-5-(Amino" and insert --Ethyl (±)-[5-[Amino--.

Signed and Sealed this

Twenty-third Day of August, 1994

Attest:

Attesting Officer

BRUCE LEHMAN

Commissioner of Patents and Trademarks